United States Patent [19]

Eidt

[11] 4,116,992

[45] Sep. 26, 1978

[54] PROCESS FOR THE SIMULTANEOUS MANUFACTURE OF DIMETHYLALUMINUM CHLORIDE AND ALKYLALUMINUM CHLORIDES

[75] Inventor: Scott H. Eidt, Seabrook, Tex.

[73] Assignee: Texas Alkyls, Inc., Deer Park, Tex.

[21] Appl. No.: 791,361

[22] Filed: Apr. 27, 1977

[51] Int. Cl.$^2$ ............................................... C07F 5/06
[52] U.S. Cl. ............................................... 260/448 A
[58] Field of Search ................................... 260/448 A

[56] References Cited

U.S. PATENT DOCUMENTS 2,270,292  1/1942  Grosse ............................. 260/448 A

OTHER PUBLICATIONS

Mole et al., Organoaluminum Compounds, Elsevier Publ. Co. N.Y., pp. 10, 30 to 32 (1972).
Coates et al. Organometallic Compounds, Methuen & Co. Ltd. London, vol. 1, pp. 297–298 (1967).
Pitzer et al., J.A.C.S. 68, 2204 (1946).
Grosse et al., J. Org. Chem. 5, 106 (1940).

Primary Examiner—Helen M. S. Sneed

Attorney, Agent, or Firm—M. Henry Heines

[57] ABSTRACT

A redistribution process for the simultaneous production of dimethylaluminum chloride and numerous alkylaluminum chlorides is described herein. The redistribution process is a chemical reaction which consists of first forming a mixture of methylaluminum dichloride and at least one alkylaluminum compound selected from the group consisting of an aluminum trialkyl, a dialkylaluminum chloride, and an alkylaluminum sesquichloride, where "alkyl" refers to a group containing 2 to 16 carbon atoms. The relative amounts of the mixture components are fixed such that the mixture has a chlorine-to-aluminum atomic ratio of 1.0 to 2.0. The mixture thus formed is next subjected to a fractional distillation, in which a first fraction is obtained, consisting of dimethylaluminum chloride, essentially free of trimethylaluminum, methylaluminum dichloride, and other impurities. The distillation residue consists essentially of alkylaluminum chlorides, which are valuable commercial materials. Dimethylaluminum chloride itself is useful as a methylating agent, a polymerization cocatalyst, a chemical intermediate, and a pyrophoric fuel.

12 Claims, No Drawings

PROCESS FOR THE SIMULTANEOUS MANUFACTURE OF DIMETHYLALUMINUM CHLORIDE AND ALKYLALUMINUM CHLORIDES

BACKGROUND OF THE INVENTION

This invention relates to a process for the manufacture of dimethylaluminum chloride, a compound known to be useful in a variety of applications. Common examples of these applications are use as a cocatalyst with transition metal compounds for the polymerization of olefins and dienes, as a methylating agent, and as a starting material for the manufacture of trimethylaluminum, a compound of considerable utility as a cocatalyst, chemical intermediate, and hypergolic fuel.

One of the known processes for the manufacture of dimethylaluminum chloride involves the reaction of methyl chloride with a special aluminum-magnesium alloy, $Al_2Mg$; C. J. Marsel, E. O. Kalil, A. Reidlinger, and L. Kramer, *Advances in Chemistry Series*, No. 23, p. 176 (1959):

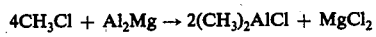

This process has the disadvantage of a high raw material cost, since the cost of the alloy is significantly higher than the cost of aluminum. Furthermore, magnesium chloride is formed as a by-product and presents disposal problems because of its physical properties and low commercial value. The use of a 70 weight % aluminum/30 weight % magnesium alloy, commercially produced by Dow Chemical Co., is also described in the reference. Unfortunately, the aluminum content of the 70/30 alloy is higher than that of $Al_2Mg$, which contains only 69 weight % aluminum. Thus, the dimethylaluminum chloride produced therefrom is contaminated with a small amount of methylaluminum dichloride.

U.S. Pat. No. 2,786,860 teaches a process for the production of organic aluminum compounds by reacting an aluminum halide or alkylaluminum halide with an alkali hydride and an olefin having a terminal double bond. This process involves a three-step reaction cycle, which must be repeated several times to obtain the desired yield, while recycling one of the by-products as a starting material.

Dimethylaluminum chloride can also be produced by reaction between trimethylaluminum and methylaluminum sesquichloride. The latter is an equimolar mixture of dimethylaluminum chloride and methylaluminum dichloride. This process also suffers from a high raw materials cost, in this case due to trimethylaluminum.

Numerous reactions are known in the art to produce alkylaluminum sesquihalides. U.S. Pat. No. 2,863,894 teaches the reaction between aluminum and a primary alkyl halide in the presence of an inert solvent. When the sesquihalide is produced, the alkylaluminum dihalide is present in 50% molar proportion, and must be separated by distillation.

Dimethylaluminum chloride is also produced by reaction of methylaluminum sesquichloride with sodium chloride (V. F. Hnizda and C. A. Kraus, *J. Amer. Chem. Soc.* 60, p. 2276 (1938). In this process, over half of the methylaluminum sesquichloride is converted to $CH_3AlCl_2 \cdot NaCl$, a complex salt of very little commercial utility which presents disposal problems because of its low solubility in organic solvents and the potential hazards due to its vigorous reactivity toward aqueous solvents.

BRIEF DESCRIPTION OF THE INVENTION

It has been discovered that dimethylaluminum chloride can be produced by a process requiring relatively inexpensive raw materials which are less pyrophoric than trimethylaluminum and which do not produce useless by-products which are difficult to dispose of. These improved results are achieved by a combination distillation/redistribution process, involving the reaction of methylaluminum dichloride and an appropriate alkylaluminum compound selected from the group consisting of trialkylaluminum, dialkylaluminum chloride, and alkylaluminum sesquichloride, in which the alkyl group contains two or more carbon atoms. The by-product of this process is a dialkylaluminum chloride, an alkylaluminum dichloride, or a mixture of the two. The composition of the by-product can be controlled by the type and quantity of the alkylaluminum compound used as a reactant.

DETAILED DESCRIPTION OF THE INVENTION

According to the process of the invention, a mixture is prepared comprising methylaluminum dichloride and an alkylaluminum compound selected from the group consisting of aluminum trialkyl, dialkylaluminum chloride, and alkylaluminum sesquichloride, in which the alkyl group contains 2 to 16 carbon atoms, preferably 2 to 6 carbon atoms, most preferably 2 to 4 carbon atoms. All carbon atom ranges stated herein are intended to be inclusive of their upper and lower limits. A solution of methylaluminum dichloride in dimethylaluminum chloride can be used in place of pure methylaluminum dichloride.

The term "alkyl" is used herein to denote a monovalent radical comprised of a straight- or branched-chain saturated alkane with one hydrogen atom removed at the point of bonding to the aluminum atom. The alkyl radical itself thus has the empirical formula $C_nH_{2n+1}$, in which n denotes the number of carbon atoms referred to above. Although combinations of different alkyl groups are possible on the same alkylaluminum compound, usually all the alkyl groups on a particular alkylaluminum compound are the same. Alkylaluminum compounds containing secondary or tertiary alkyl groups are not as preferred as those containing straight- or other branched-chain alkyl groups since the former are not as readily available or as stable as the latter. Particularly preferred alkylaluminum compounds are triethylaluminum, diethylaluminum chloride, ethylaluminum sesquichloride, triisobutylaluminum, diisobutylaluminum chloride, and isobutylaluminum sesquichloride. Of these, the most preferred are triethylaluminum, diethylaluminum chloride, ethylaluminum sesquichloride, and triisobutylaluminum.

The mixture is placed in an efficient distillation column in which association and alkyl interchange occur simultaneously with the migration of the various system components throughout the column. In the association and alkyl interchange, i.e., the redistribution reaction, neighboring molecules exchange and redistribute their aluminum substituents to produce molecules with new substituent combinations. The quantities and types of the different combinations produced thereby are controlled by the chemical equilibrium of the reaction. The migration referred to above is the common result of the distillation process, brought about by the simultaneous vaporization and condensation of each component as the system seeks to achieve thermal equilibration throughout the length of the column. The distillation column promotes the migration of the lower boiling components to the uppermost portions of the column, and the higher coiling components to the lower portions of the column. Thus, thermal and chemical driving forces combine to place the lowest boiling component at the uppermost end of the column. Removal of this component results in an imbalance in the chemical equilibrium at the top of the column, which the redistribution process seeks to overcome by producing more of the same low boiling component. In a system containing both methyl and higher alkyl substituents, the methyl substituted components are generally lower boiling that the higher akyls. The redistribution process in such a system continues until essentially all of the methyl groups have passed out of the top of the column in the form of the lowest boiling component.

When bromides or iodides are used as either of the two starting materials, the lowest boiling component in the column is trimethylaluminum. Thus, when the redistribution process is practiced with bromides or iodides, the component that predominates at the top of the distillation column and escapes through the vapor phase is trimethylaluminum. Owing to the substantial boiling point difference between trimethylaluminum and the next lowest boiling component, dimethylaluminum bromide or iodide, trimethylaluminum can be obtained by such a process in a highly pure state. This process is described in detail in co-pending application Ser. No. 455,448, the subject matter of which is incorporated herein by reference. When chlorides are used, however, the product of pure trimethylaluminum is hindered by the fact that its boiling point is extremely close to that of dimethylaluminum chloride. Separation of two such components whose boiling points are in such proximity would be virtually impossible.

It has been discovered, however, that in the process of the invention, the reaction can be substantially controlled to produce a highly pure dimethylaluminum chloride, substantially free of trimethylaluminum, rather than a co-distilling mixture of the two. This result is achieved when the atomic ratio of chlorine to aluminum in the system is between about 1.0 and about 2.0, as will be more fully explained hereinbelow.

In the case of halides other than chlorides, trimethylaluminum is formed to some extent at all halogen/aluminum atomic ratios. The low boiling point of trimethylaluminum renders it capable of removal from non-chloride systems by fractional distillation. Extending this to chloride systems, one would expect attempts at distillation to result in a co-distilling mixture of trimethylaluminum and dimethylaluminum chloride, since the two are incapable of separation by distillation. The present invention, however, lies in the discovery that the proper manipulation of the Cl/Al ratio will result in the lack of formation of trimethylaluminum. Thus, the process can be used to produce highly pure dimethylaluminum chloride by maintaining the Cl/Al ratio in the reactants (on an atomic basis) between about 1.0 and about 2.0. A preferred range of the Cl/Al atomic ratio is about 1.0 to about 1.5. Improved yields are obtained within this preferred range. The Cl/Al range limits are specified in approximate terms in order to incorporate the flexibility made necessary by systematic errors in both measurement techniques and detection limits.

Within these limits, further control of the Cl/Al ratio can be used to control the resulting by-product formed along with the dimethylaluminum chloride. For example, by using the appropriate combination of reactants, either an alkylaluminum dichloride, a dialkylaluminum chloride, or an alkylaluminum sesquichloride (an equimolar mixture of the two) can be produced. Equations illustrating possible variations are shown below. For the purpose of illustration, methylaluminum sesquichloride is used in place of methylaluminum dichloride. The former is an equimolar mixture of methylaluminum dichloride and dimethylaluminum chloride, and has the formula $(CH_3)_3Al_2Cl_3$. It is used for two reasons. First, the sesquichloride has a melting point of 23° C., and is thus much easier to handle and transfer than methylaluminum dichloride, which has a melting point of 73° C. Second, the sesquichloride is readily prepared from inexpensive starting materials, methyl chloride and aluminum, by the following reaction:

Some of the possible variations of reactants and products are as follows:

Starting with alkylaluminum sesquichloride:

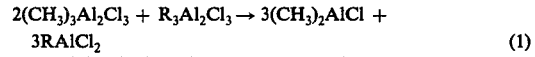

Starting with dialkylaluminum chloride:

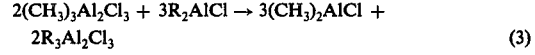

Starting with aluminum trialkyl:

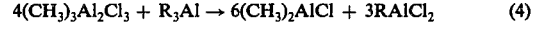

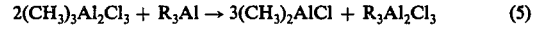

Note that in Reactions (1) through (6), the Cl/Al ratio is between 1.0 and 2.0.

At a given pressure, the operating temperature will span the entire range encountered in the distillation column, from the low temperature of the vapor at the uppermost part of the column to the high temperature of the liquid in the still pot. There are no restraints on the operating temperatures and pressures other than their mutual dependence due to the boiling state. For convenient operation, however, the pressure will be between about 0.01 Torr and about 4.0 atmospheres. At these extremes, the column temperatures will range from about −20° C. to about 200° C. Subatmospheric pressures are preferred for ease of reaction control and to insure that still pot temperatures are below the thermal decomposition temperatures of the akylaluminum compounds. A pressure range from about 20 Torr to about 180 Torr, with distillation temperature dependent thereon, is particularly preferred. At these pressures, the boiling range of dimethylaluminum chloride, and thus the uppermost column temperature is about 32° C. to about 80° C. While the temperatures of the dimethylaluminum chloride vapor remains essentially unchanged throughout a distillation carried out at constant pressure, the temperature of the pot liquid gradually increases due to the increase in concentration of the higher boiling components. The pot temperature further depends on the type and relative amount of alkylaluminum compound used as a starting material. In addition, the differential between the vapor and pot temperatures broadens with increasing system pressure.

The initial step in the Redistribution Process consists of the mixing of the methylaluminum dichloride and the appropriate alkylaluminum compound in a reaction vessel containing an inert atmosphere. The vessel may be the distillation still pot used in the next step. The methylaluminum dichloride or sesquichloride may either be prepared separately or in the presence of the alkylaluminum compound. In the latter case, the methyl chloride is charged to a stirred suspension of activated aluminum in the alkylaluminum compound. The heat generated by this reaction, which is normally carried out at slight super-atmospheric pressures, is much greater than that produced by mixing the alkylaluminum compound and previously prepared methylaluminum chloride of sesquichloride. Under the conditions of the Redistribution Process, no readily detectable reaction occurs between the methyl chloride and the alkylaluminum compound.

In the second step, the redistribution reaction proceeds in a practical manner. An efficient fractioning column provides the conditions which promote the redistribution process. An efficient fractional distillation column is defined as a column capable of distilling pure dimethylaluminum chloride from a mixture composed of dimethylaluminum chloride and an alkylaluminum chloride having a boiling point at atmospheric pressure that is higher than that of dimethylaluminum chloride. Examples of such an efficient column are a packed column, a bubble cap tray column and a spinning band column. In the upper portions of the column, where the more volatile components are concentrated, the environment favors the formation of dimethylaluminum chloride. Since it is more volatile than the other components, dimethylaluminum chloride escapes the liquid surface and is no longer subject to redistribution. Dimethylaluminum chloride that is essentially free of impurities can be obtained by using an efficient column and a high reflux ratio. The yield of dimethylaluminum chloride is in the range of 80–98% of theory.

After the removal of the high purity dimethylaluminum chloride fraction, a small intermediate fraction is distilled. This fraction, primarily a mixture of dimethylaluminum chloride and methylaluminum dichloride, contains the majority of the methyl groups which remained after the distillation of the pure dimethylaluminum chloride. In a commercial process this fraction would be recycled.

The residual still pot liquid has a low methylaluminum content, and contains substantially all the alkyl groups from the alkylaluminum compound originally charged. Thus, dependent upon the molar ratio and type of reactants used, the residual still pot liquid is substantially pure dialkylaluminum chloride, alkylaluminum sesquichloride, or alkylaluminum chloride. Most of these compounds are liquids, while some are solids that have melting points slightly higher than ambient temperature. Though all are significantly less volatile than the methylaluminum chlorides, some have boiling points at subatmospheric pressures which are sufficiently low to permit distillation without decomposition.

The process described in this invention possesses distinct advantages over other processes for the production of dimethylaluminum chloride. One advantage is the simplicity of the process equipment used. Because the reactants and products are compounds which are liquid at ambient or slightly above ambient temperature, these materials are easily transferred, via piping or tubing, from one vessel to another. The reaction vessels do not require the powerful, efficient and expensive agitators which are necessary in processes wherein a reactant and/or reaction product are solids. No expensive or complex filtration apparatus or other solids-handling equipment is necessary. Some of the other processes for the preparation of dimethylaluminum chloride use less expensive starting materials than those required in the Redistribution Process, but the Redistribution Process has the advantage of producing commercially valuable by-products.

The above described invention can be further understood by the following specific examples.

EXAMPLE 1

This example describes the preparation of dimethylaluminum chloride and diethylaluminum chloride, according to the mechanism of Reaction (6) above, whereby equimolar quantities of methyl-aluminum sesquichloride and triethylaluminum, which produce a mixture with a Cl/Al atomic ratio of 1.00, are combined as follows:

$$2(CH_3)_3Al_2Cl_3 + 2(C_2H_5)_3Al \rightarrow 3(CH_3)_2AlCl + 3(C_2H_5)_2AlCl$$

The reactor consisted of a one-liter, heavy-walled, three-necked glass flask to which were attached a thermowell, addition funnel, and vacuum-jacketed distillation column. The distillation column had an inner diameter of 20 mm and was packed to a height of about 90 cm with stainless steel packing. A distillation head at the top of the column with a variable reflux ratio was connected to a distillate receiver system and a nitrogen-vacuum source.

To 417.0 g (2.03 moles) of methylaluminum sesquichloride in the reactor were added 232.3 g (2.03 moles) of triethylaluminum over a period of ten minutes, during which time the temperature of the mixture increased from 30° C. to 50° C. The mixture was stirred and heated and vacuum was applied to maintain the system pressure at 40 Torr. When a rapid reflux rate was attained in the distillation head the temperatures were 44.0° C. and 92.0° C. in the vapor and pot liquid, respectively. The heat to the still pot was gradually increased and the reflux ratio was set at 10. Two fractions of distillate were collected and, along with the residue, were analyzed for Cl/Al ratios and methyl and ethyl contents by hydrolysis. The results are listed below.

| Fraction Number | Wt. (g) | Boiling Range (° C) | Analysis (weight %) | | | |
|---|---|---|---|---|---|---|
| | | | DMAC[a] | MADC | DEAC | EADC |
| 1 | 270.2 | 44.0–44.4 | 99.7 | 0.3 | — | — |
| 2 | 25.0 | 47.0–80.0 | 22.2 | 2.2 | 69.5 | 6.1 |
| Residue | 325.0 | — | — | — | 98.4[b] | — |

[a]DMAC: $(CH_3)_2AlCl$
MADC: $CH_3AlCl_2$
DEAC: $(C_2H_5)_2AlCl$
EADC: $C_2H_5AlCl_2$
[b]Remainder consisted of redistribution products of impurities initially present in $(C_2H_5)_3Al$ starting material.

The data indicate that trimethylaluminum is not produced in this process.

EXAMPLE 2

This example illustrates the effect of using a system where the Cl/Al ratio is less than 1.00. The procedure is similar to that of Example 1, except that 100% molar excess of triethylaluminum is used, as shown in the equation below, resulting in a mixture having a Cl/Al ratio of 0.75:

$$2(CH_3)_3Al_2Cl_3 + 4(C_2H_5)_3Al \rightarrow 3(CH_3)_2AlCl + 3(C_2H_5)_2AlCl + 2(C_2H_5)_3Al$$

The experimental appratus was the same as that used in Example 1. To 414.9 g (2.02 moles) of methylaluminum sesquichloride stirred at 30° C. in the reactor were added 463.3 g (4.04 moles) of triethylaluminum. The system pressure was lowered to 40 Toor and the still pot contents were heated to boiling. At the attainment of a rapid reflux rate in the distillation head, the vapor and liquid phase temperatures were 42.4° C. and 104° C., respectively. As the pot temperature gradually rose from 104° C. to 122° C., five fractions of distillate were collected at a reflux ratio of 10. Analysis of these fractions and the residue are listed below:

| Fraction No. | Wt. (g) | Boiling Range (° C) | Analysis (weight %) | | | |
|---|---|---|---|---|---|---|
| | | | TMAL[a] | DMAC | TEAL | DEAC |
| 1 | 22.1 | 42.5 – 44.0 | 9.3 | 90.7 | — | — |
| 2 | 167.9 | 43.9 – 44.2 | 9.3 | 90.7 | — | — |
| 3 | 30.9 | 43.8 – 44.1 | 9.3 | 90.7 | — | — |
| 4 | 28.1 | 44.0 – 69.0 | 9.4 | 86.7 | 0.5 | 3.3 |
| 5 | 16.8 | 70.0 – 88.0 | 4.6 | 36.9 | 7.6 | 50.9 |
| Residue | 578.5 | — | 0.1 | — | 33.1 | 66.8[b] |

[a]TMAL: (CH$_3$)$_3$Al
DMAC: (CH$_3$)$_2$AlCl
TEAL: (C$_2$H$_5$)$_3$Al
DEAC: (C$_2$H$_5$)$_2$AlCl
[b]Impurities also present as in Example 1.

Comparison of the above results with those of Example 1 show that a substantial quantity of trimethylaluminum is produced as a result of the lower Cl/Al ratio. This component is inseparable from the desired dimethylaluminum chloride by distillation. The trimethylaluminum can be converted to the desired dimethylaluminum chloride by addition to the mixture of the appropriate calculated quantity of the starting material, methylaluminum sesquichloride by the following reaction:

$$(CH_3)_3Al + (CH_3)_3Al_2Cl_3 \rightarrow 3(CH_3)_2AlCl$$

EXAMPLE 3

In this example, dimethylaluminum chloride and isobutylaluminum sesquichloride are prepared from methylaluminum sesquichloride and trisobutylaluminum, according to the mechanism of Reaction (5) above, with a Cl/Al atomic ratio of 1.20:

$$2(CH_3)_3Al_2Cl_3 + (iso-C_4H_9)_3Al \rightarrow 3(CH_3)_2AlCl + (iso-C_4H_9)_3Al_2Cl_3$$

In the same type of reactor as that described in Example 1, 199.8 g (1.01 moles) of triisobutylaluminum were added to 415.0 g (2.02 moles) of methylaluminum sesquichloride with stirring at 80°-90° C. over a period of 20 minutes. The system pressure was adjusted to 40 Torr and heat was applied. At vigorous reflux, the vapor and liquid temperatures were 44.0° C. and 90.0° C., respectively. Four distillate fractions were collected at a reflux ratio of 10. Analysis of each, together with that of the residual still pot liquid, is shown below.

| Fraction Number | Wt. (g) | Boiling Range (° C) | Analysis (weight %) | | | |
|---|---|---|---|---|---|---|
| | | | Dmac[a] | Madc | Dibac | Ibadc |
| 1 | 238.0 | 43.8 – 44.2 | 99.3 | 0.7 | — | — |
| 2 | 18.2 | 44.0 – 45.0 | 99.3 | 0.7 | — | — |
| 3 | 11.6 | 45.1 – 45.8 | 99.3 | 0.7 | — | — |
| 4 | 8.7 | 46.0 – 59.0 | 48.5 | 51.5 | — | — |
| Residue | 312.9 | — | 1.2 | — | 57.3 | 41.2[b] |

[a]DMAC: (CH$_3$)$_2$AlCl
MADC: CH$_3$AlCl$_2$
DIBAC: (iso-C$_4$H$_9$)$_2$AlCl
IBADC: iso-C$_4$H$_9$AlCl$_2$
[b]Impurities present as in Example 1.

Thus, the preparation of substantially pure dimethylaluminum chloride, free of trimethylaluminum, is illustrated.

EXAMPLE 4

This example illustrates the use of a high Cl/Al atomic ratio. Dimethylaluminum chloride and ethylaluminum dichloride were prepared by a process similar to Reaction (1) above, except that methylaluminum dichloride was used as a starting material in place of methylaluminum sesquichloride. Hence, the reaction was as follows, with a starting mixture having a Cl/Al ratio of 1.75:

$$2CH_3AlCl_2 + (C_2H_5)_3Al_2Cl_3 \rightarrow (CH_3)_2AlCl + 3C_2H_5AlCl_2$$

In the same type of reactor as that described in Example 1, 500.5 g (2.02 moles) of ethylaluminum sesquichloride were added to 456.2 g (4.04 moles) of methylaluminum dichloride with stirring at 80° C. over a period of ½ hour. At 40 Torr system pressure and rapid reflux, three distillate fractions were collected at a reflux ratio of 10, as indicated below.

| Fraction Number | Weight (g) | Boiling Range (° C) |
|---|---|---|
| 1 | 56.5 | 43.7 – 43.8 |
| 2 | 76.1 | 43.8 – 45.6 |
| 3 | 34.4 | 50.0 – 58.6 |
| Residue | 751.1 | — |

While the intial 71% of the methyl groups originally charged to the still pot appeared in the distillate, the distillate composition in weight percent was 99% DMAC and 1% MADC (abbreviations identical to Example 1). As more of the methyl groups were distilled over, the MADC/DMAC ratio in the distillate increased markedly. When 86% of the methyl group charge had been distilled the total distillate consisted of 92 wt% DMAC and 8 wt% MADC. The quantity of DMAC of this purity that was distilled corresponding to 90% of the theoretical yield of pure DMAC.

As a result of the incomplete distillation of the DMAC, the residual still pot liquid was not the desired high purity EADC. Instead, the approximate composition (wt%, calculated from analytical data) of this liquid was: EADC-90, MADC-5, and DEAC-5.

Im summary, the experiment shows that, starting with a mixture in which Cl/Al atomic ratio is as high a 1.75, the redistribution process produces a moderate yield of DMAC that is practically free of MADC. A much larger quantity of DMAC-rich distillate can be obtained, but at the expense of DMAC purity.

With regard to the above examples, it will be readily apparent to one skilled in the art that higher purities can be achieved with a longer and more efficient distillation column, as well as a higher reflux ratio.

What is claimed is:

1. A redistribution process for the production of dimethylaluminum chloride and alkylaluminum chlorides comprising forming a mixture comprising methylaluminum dichloride and at least one alkylaluminum compound selected from the group consisting of an aluminum trialkyl, a dialkylaluminum chloride, and an alkylaluminum sesquichloride, in which the alkyl group contains from 2 to 16 carbon atoms, such mixture having a chlorine-to-aluminum atomic ratio of from about 1.0 to about 2.0, and distilling said mixture in an efficient distillation column to effect separation of said mixture into a first fraction consisting essentially of dimethylaluminum chloride and a residue of alkylaluminum chlorides.

2. The process of claim 1 in which the alkyl groups of the alkylaluminum compound consist of alkyl radicals containing from 2 to 6 carbon atoms.

3. The process of claim 1 in which the alkyl groups of the alkylaluminum compound consist of alkyl radicals containing from 2 to 4 carbon atoms.

4. The process of claim 1 in which the distillation is conducted at a pressure of from about 0.01 Torr to about 4.0 atmospheres.

5. The process of claim 1 in which the distillation is conducted at a subatmospheric pressure.

6. The process of claim 1 in which the distillation is conducted at a pressure of from about 20 Torr to about 180 Torr.

7. The process of claim 1 in which the alkylaluminum compound is selected from the group consisting of triethylaluminum, diethylaluminum chloride, ethylaluminum sesquichloride, triisobutylaluminum, diisobutylaluminum chloride, and isobutylaluminum sesquichloride.

8. The process of claim 1 in which the chlorine-to-aluminum atomic ratio is from about 1.0 to about 1.5.

9. The process of claim 1 in which the alkylaluminum compound is selected from the group consisting of triethylaluminum, diethylaluminum chloride, ethylaluminum sesquichloride, and triisobutylaluminum.

10. The process of claim 1 in which the alkylaluminum compound is triethylaluminum.

11. The process of claim 1 in which the alkylaluminum compound is ethylaluminum sesquichloride.

12. The process of claim 1 in which the alkylaluminum compound is diethylaluminum chloride.

* * * * *